United States Patent [19]

Schaus et al.

[11] Patent Number: 5,273,050
[45] Date of Patent: Dec. 28, 1993

[54] ECG ANALYSIS SYSTEM WITH MULTIPLE CASSETTE LOADER

[76] Inventors: Anthony Schaus, 23872 Gates St., Lake Forest, Calif. 92630-2929; Arvind C. Desai, 28442 Munera, Mission Viejo, Calif. 92692; John Cater, 24 Acorn, Irvine, Calif. 92714; John A. Bachman, 24372 Armada Dr., Dana Point, Calif. 92629; Wilber David Squires, 8612 El Rancho, Fountain Valley, Calif. 92708

[21] Appl. No.: 789,089

[22] Filed: Nov. 7, 1991

[51] Int. Cl.⁵ .......................................... A61B 5/0432
[52] U.S. Cl. .................................................. 128/702
[58] Field of Search ...................... 128/702, 710, 711; 304/413.02, 413.06

[56] References Cited

U.S. PATENT DOCUMENTS

| | | | |
|---|---|---|---|
| 4,073,011 | 2/1978 | Cherry et al. | 128/711 |
| 4,098,267 | 7/1978 | Stein et al. | 128/711 |
| 4,999,772 | 3/1991 | Bowman et al. | 128/711 |

OTHER PUBLICATIONS

Cower et al., "Computers in Cardiology Conference", Rotterdam Netherlands, Sep.24-Oct. 1, 1977, pp. 497-501.

Primary Examiner—William E. Kamm

[57] ABSTRACT

An ECG analysis system is provided that automatically scans and classifies in sequence a plurality of long term recorded patient cassette tapes by first identifying and then inserting each tape cassette into a cassette player for the analysis system, and finally removing each tape cassette from the analysis system once the analysis is complete. The system includes bar code reading and writing devices that are integrated with the analysis system to positively identify the patient associated with the tape recording. An automatic multiple cassette loader is disclosed wherein an elongated, rigid transport member having a transport slot cut along a substantial portion of its longitudinal axis is used to guide a detent armature, driven by a worm drive, in placing cassettes within a cassette player. The detent armature protrudes through said transport slot and pushes a single cassette out from the bottom of a stack of cassettes along the longitudinal axis of the transport slot and into the cassette player. Cassette removal is accomplished by a pair of jointed members coupled to motor means and a release mechanism within the playback means to eject the cassette from the playback means at a predetermined time. A pair of armatures are rotatably attached to the placement means for removing the ejected cassette from the playback means. A bay is provided into which the analyzed tape cassettes are automatically stacked.

19 Claims, 7 Drawing Sheets

ECG ANALYSIS SYSTEM WITH MULTIPLE CASSETTE LOADER

BACKGROUND OF THE INVENTION

1. Field of the invention

This invention relates to electrocardiographic (ECG) systems that can sequentially identify, analyze, and classify multiple ECG recordings, and more specifically, to ECG analysis systems having mechanisms that automatically load, read, classify and remove cassette tapes, to and from, an ECG analysis system, while placing patient data on each report for identification purposes.

2. Description of the Prior Art

The analysis of ECG recordings within the prior art has substantially improved throughout the years by an apparent unrelenting improvement in the sophistication of analysis system available within the industry. Conventional ECG ambulatory (Holter) monitoring employs a magnetic tape recorder and sensing devices for recording the bioelectric signals of the human heart. The recording sessions may last up to twenty-four hours or more. Thus analysis is only practical at speeds significantly greater than the real time recording speed. Typically, analysis takes place at 120 to 240 times the actual recording speed. Recent developments in computers and Digital Signal Processing (DSP) techniques have made possible scanning speeds of 500 times the real time recording speed, or even higher. Numerous methods have been used to automate to identify various cardiac abnormalities within the recording. Prior systems may either interact with the user or automatically keep record of the abnormalities existing within a recording. However, no system is readily available that can analyze multiple ECG recordings in a batch mode. Thus, there is a shortcoming within the prior art due to the lack of teachings wherein multiple recordings are automatically loaded, identified, analyzed and classified by the system without the need for user interaction. It is this shortcoming that is addressed by the present invention.

SUMMARY OF THE INVENTION

An ECG analysis system is provided that automatically scans multiple ECG cassette tapes containing recorded ECG data, on an individual basis, by use of a multiple cassette loader that inserts cassette tapes into playback means to input ECG data into the analysis system, and that removes each cassette tape from the analysis system once analysis is complete. The system includes digital computational means that converts data from the cassette tape player into a digital format and performs an arrhythmia analysis on the recorded data received.

The multiple cassette loader is formed from an elongated, rigid transport member that contains a transport slot along a substantial portion of its longitudinal axis. Stack holding means are fixedly attached to the transport member distal to the cassette player. The stack holding means stacks a plurality of cassette tapes which the transport member guides into placement by means of a detent armature driven by a worm drive. The detent armature protrudes through the transport slot to push a single cassette from the bottom of the stack of cassette tapes, contained in stack holding means, along the longitudinal axis of the transport member and into the cassette player as a result of worm drive motor initiating movement through the worm drive. The cassette is guided in the movement into the cassette player by parallel rails, on either side of the transport member between the stack holding means and cassette player. The system includes an infer-red bar code reading device situated below the stack holding means that scans the bar code label on each cassette and provides the analysis system with patient identification.

Tape cassette removal is accomplished by a pair of jointed members coupled to ejection motor means that operate to eject cassette tape when signaled by analysis system. A pair of cam mounted pincher arms then attach to the ejected cassette and retrieve the cassette from the cassette player. The pincher arms are rotatably attached to the placement means and move with the placement means in forward and reverse directions under the control of worm drive in cooperation with the detent armature. A bay is provided to stack the analyzed tapes.

The system analyzes each of the cassette tapes to identify the presence of clinically significant abnormalities within the recorded ECG data. A report is generated for each patient recording to enable those patient recordings containing benign ECG data to be segregated from those that require further analysis.

It is an object of the present invention to provide a device that is capable of analyzing a plurality of recorded patient ECG cassette tapes without user invention.

It is further an object of the present invention to provide an apparatus capable of identifying those recordings that do not contain significant cardiac abnormalities so that those recordings can be segregated from recordings requiring further analysis.

It is a further object of this invention to provide an apparatus that automatically plays back in sequence multiple cassette tapes having recordings of cardiac patients and supplies the data recorded, thereon, to an analysis and analysis reporting system.

It is a further object of the invention to provide a multiple tape scanning apparatus that positively identifies patient tapes, thereby, avoiding mistakes in the handling of multiple tape results be the analysis system.

It is a further object of the invention to provide an apparatus that can automatically handle multiple cassette tapes, contained in a stack, in sequence and provide data recorded, thereon, into a computer for analysis.

It is a further object of the invention to provide an apparatus that automatically restacks tape cassettes after playback of the tapes in sequence.

It is further an object of the invention to provide a device capable of multiple cassette insertion and removal under computer control.

DETAILED DESCRIPTION OF THE PREFERRED EMBODIMENT

Figure 1:
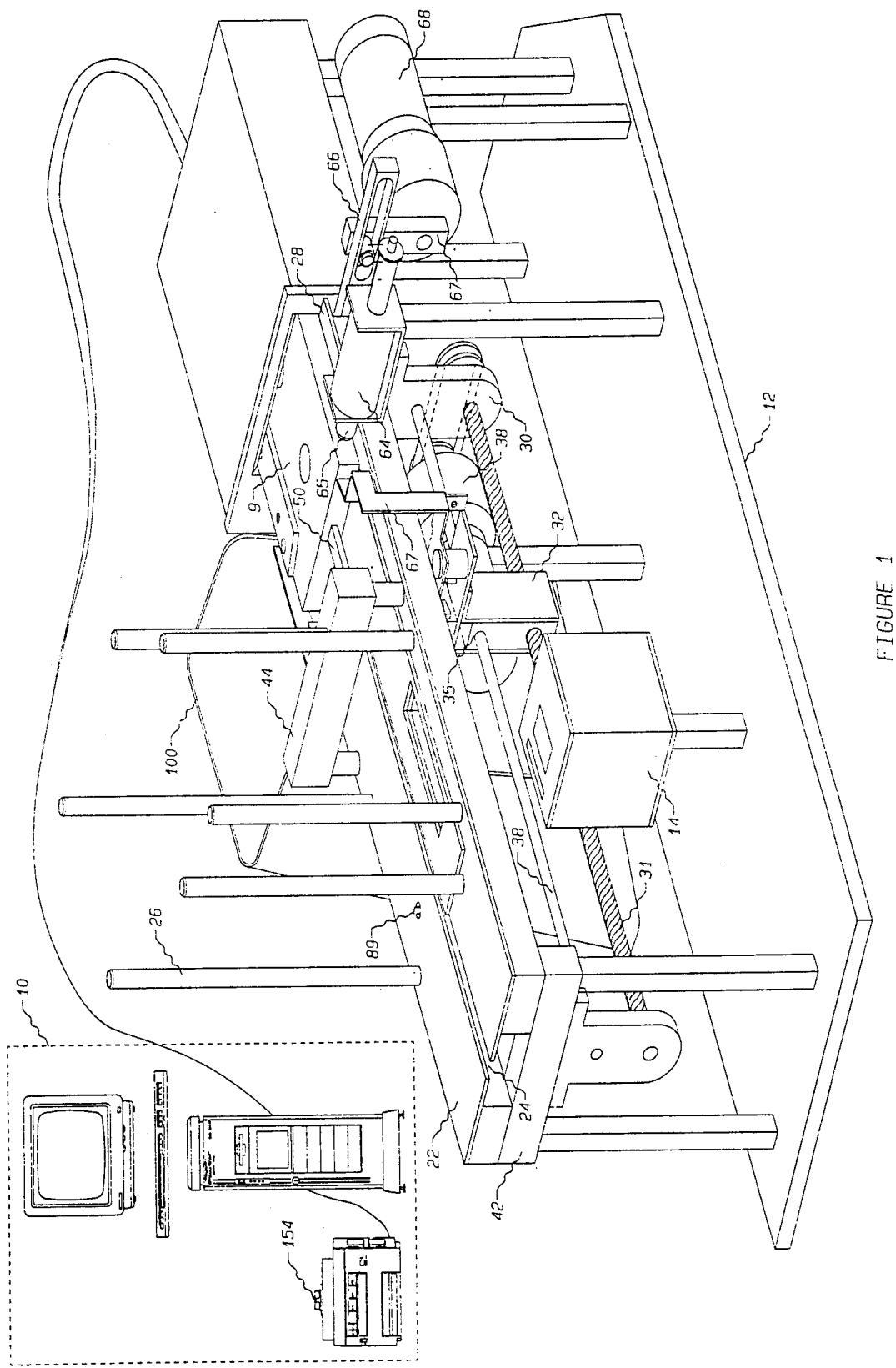
FIG. 1 is an isometric view of the invention.

The invention as shown in FIG. 1 which is an isometric view of an electrocardiographic (ECG) analysis system 10 with cassette player 70 having a multiple cassette loader 20 used to insert and remove any of a plurality of cassette tapes 8 into cassette player 70. ECG analysis system 10 automatically scans a single cassette 9 taken from a plurality of cassette tapes 8, individually, by inserting single cassette tape 9 into cassette player 70 for the analysis system, and removes each cassette tape 9 from the analysis system once analysis is complete. The system includes digital computer 16 that receives data from the cassette player 70 in a digital format and a printer 154 that prints reports based on the analysis done by computer 16. The computer 16 performs arrhythmia and other ECG analysis functions on the recorded data received from cassette player 70 and stores results that can later be printed by printer 154.

The multiple cassette loader 20 is used to insert tapes into cassette player 70 and to retrieve and restack ejected tapes from cassette player 70 after they have been read. Multiple cassette loader 20 consists of an elongated, rigid transport member 22 containing transport slot 24 along a substantial portion of its longitudinal axis. Stack holding means 26 are fixedly attached to the transport member 22 at the end distal to cassette player 70. The stack holding means are capable of stacking a plurality of cassette tapes 8. Transport member 22 is used to guide placement of cassette 9 by a detent armature 50 driven by a worm drive 30. The detent armature 50 protrudes through transport slot 24 to push a single cassette 9, from the bottom of the plurality of cassette tapes 8, along the longitudinal axis of the transport member 22 and into cassette player 70 as a result of worm drive motor 38 initiating the movement under the control of worm drive 30. The cassette 9 is guided in the movement into cassette player 70 by parallel rails 28, 29 on either side of the transport member 22 between the stack holding means 26 and cassette player 70. The system 10 includes a bar code device 14 capable of reading bar code on the cassettes. Bar code device 14 is situated below transport slot 24, directly underneath the stack holding means 26 and is integrated with the analysis system to positively identify the patient undergoing automatic analysis as well as identifying the attending physician.

Figure 2A:
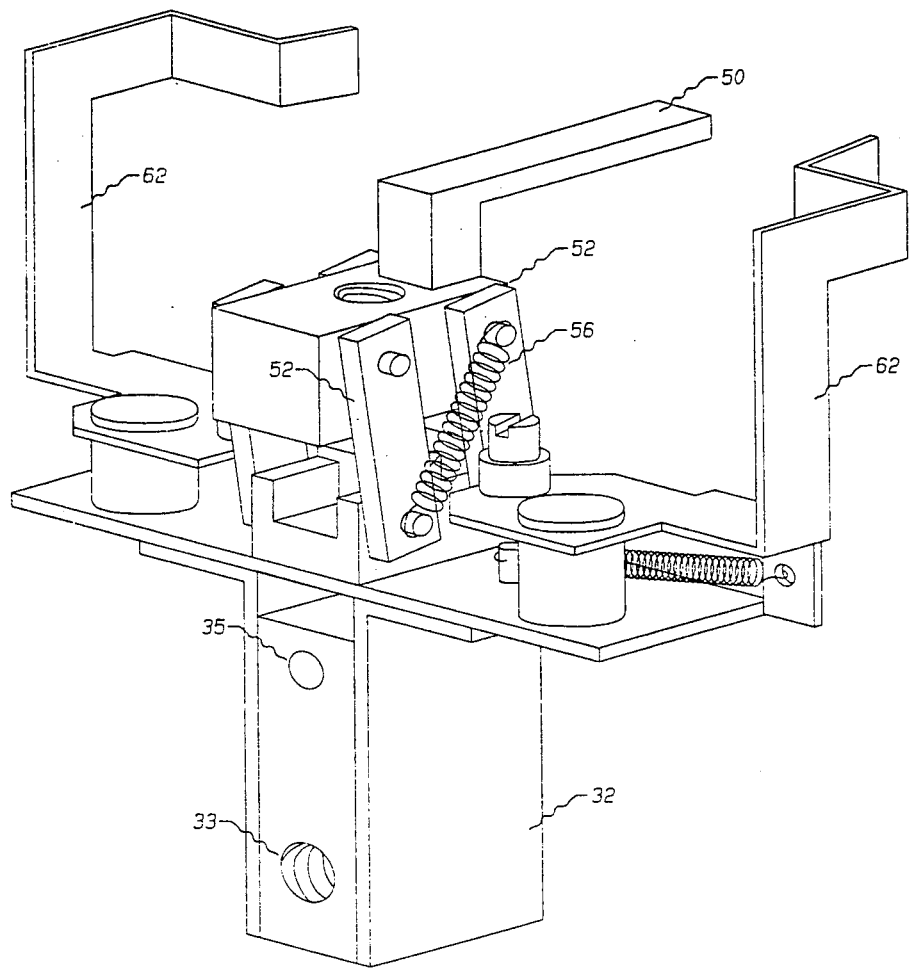
FIG. 2A is an enlarged view of the detent armature and cam mounted pincher arm assembly as driven by a worm drive.

Referring to FIG. 2A, an enlarged view of detent armature 50 assembled with cam mounted pincher arms 62, 63 in conjunction with FIG. 1, the detent armature 50 and cam mounted pincher arms 62, 63 are mounted to worm nut 32. Worm nut 32 has internal female threaded aperture 33 compatible with male threads 31 in worm drive 30, to enable the translation of rotational motion of worm drive 30 into a linear motion of the worm drive nut 32 along the male threads 31 of worm drive 30. This same linear motion is then given to detent armature 50 which is geared to be in an extended position as it travels in a forward direction towards cassette player 70 from the distal end of transport member 22. Detent armature 50 is also geared to be in a retracted position traveling in a reverse direction away from cassette player 70. Guide rod aperture 34 is contained within the body of worm nut 32 so that guide rod 35 may freely pass. Worm drive nut 32 is used to hold an assembly containing detent armature 50 and cam mounted pincher armatures 60, 61. Cam mounted pincher arms 62, 63 are mounted to worm drive nut 32 to sit above transport member 22, and detent armature 50 is mounted such that it protrudes through longitudinal slot 24 to engage a single cassette 9 contained within the plurality of cassette tape 8 during forward movement of detent armature 50 towards cassette player 70.

Figure 2B:
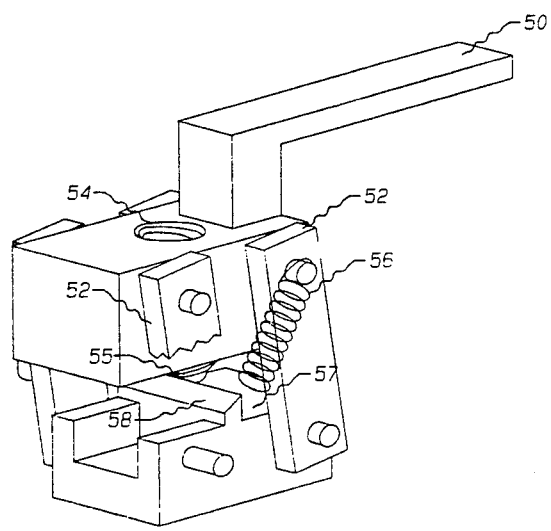
FIG. 2B is a cutaway view of the detent armature mounted on a four bar linkage.

Referring now to FIG. 2B with reference to FIG. 1, detent armature 50 protrudes through longitudinal slot 24 in an extended position, which is controlled by detent screw 54 having captured bearing 55 at the base of screw 54 acting in cooperation with and sitting on top of ridge 57 to secure detent armature 50 in the extended position. Captured bearing 55 will lock screw 54 into the extended position when worm nut 32 traverses the entire length of the male threads 31 of worm drive 30 to abut against rear cross member 42. At this point, worm nut 32 is forced against rear crossbar member 42 which in turn forces bearing 55 to travel up ramp 58 over ridge 57 and lock into place Detent armature 50 will remain in this extended position as it traverses the length of transport member 22 toward cassette player 70, during which travel, detent armature 50 will push a single cassette 9 from the bottom of the stack of a plurality of cassettes 8 and along transport member 22 into cassette player 70. Overhead cross bar member 44 permits only a single cassette tape 9 to be removed from the bottom of the plurality of cassette tapes 8. Worm drive 30, under the control of ECG analysis system 10, will control detent armature 50 to push single cassette tape 9 into cassette player 70 and a small distance further, thereby, forcing captured bearing 55 to become dislodged from ridge 57 and enabling the spring force exerted by Spring 56 to force four bar linkage 52 to retract detent armature 50. Detent armature 50 remains retracted until worm nut 32 once again traverses the entire distance of the male threads 31 and abuts against rear cross bar member 42. Thus, retracted detent armature 50 will remain retracted within the transport slot 24 until after it passes beneath stack holding means 26 and, thereby, not engage any cassette within stack holding means 26.

Figure 3:
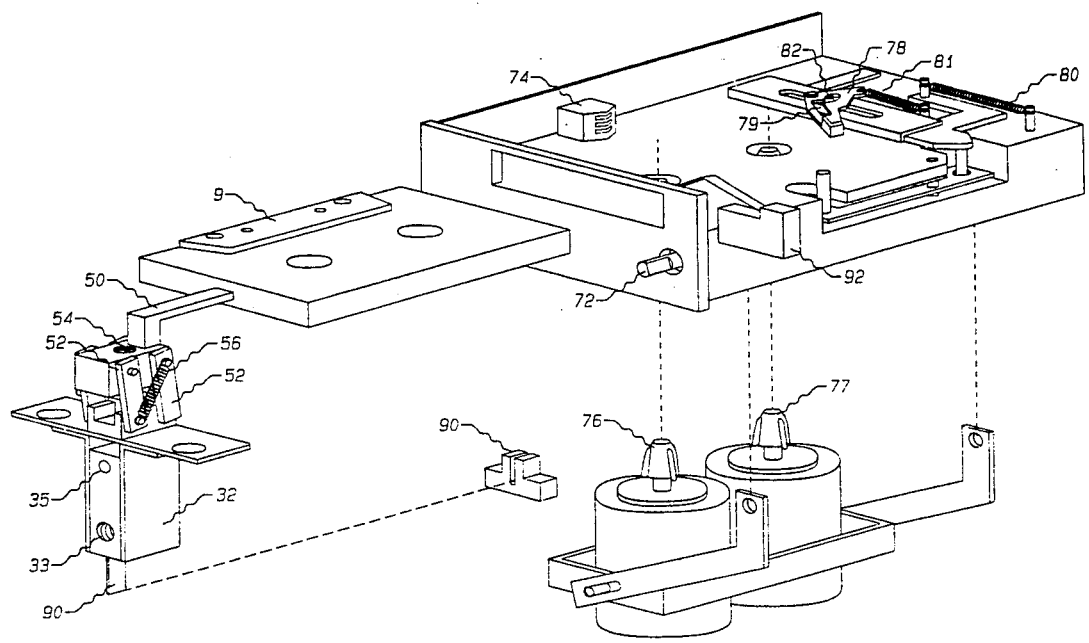
FIG. 3 is an exploded view showing the relationship of the detent armature assembly contained on a worm nut with the type of cassette player used in the preferred embodiment and the cassette drive spindles.

Now referring to FIG. 3 in conjunction with FIG. 1, cassette player 70, used within the preferred embodiment has various features not found in ordinary cassette players. These features while not actually novel, do add a quantum of uniqueness to the invention. Included are features for high speed tape playing as well as multiple speed selection. Also, rotational shaft 72 operates the loading, playing and ejecting of cassette tapes in contradistinction to the push button mechanisms usually employed in cassette players to eject cassette tapes. The present invention, by employing a cassette player having shaft 72 ensures that substantial force is used to hold the single cassette tape 9 in juxtaposition against tape head 74. In cassette players having variable speed drive spindles 76, 77, especially when using high speeds, it is necessary to have a very deliberate method of placing the cassette against tape heads 74, with a force that is substantial enough to hold the cassette positioned against tape head 74 during high speed operation. This force is found, within cassette player 70 used within the present invention, by shaft 72 applying a force to cassette 9 that is significantly more substantial than forces found in ordinary cassette players. Thus, in the present invention, shaft 72 is operated by jointed members 66, 67 under control of ejection motor 68, to place a clockwise force upon shaft 72 for the loading of cassette tape 9. This force is applied under control of digital computer 16 during a cassette loading operation.

The internal operation of cassette player 70 can be seen by referring to FIG. 3 in conjunction with FIG. 1. Here, cassette 9 is shown outside cassette player 70 waiting to be inserted into cassette player 70 by detent armature 50. Detent armature 50 will push cassette 9 into cassette player 70 such that cassette 9 will press against cassette armature 78 and force cassette armature 78 to slide around control post 82 which is contained within right angle slot 79. Once cassette 9 has forced post 82 to slide past the right angle within slot 79, insertion spring 80 will pull cassette armature 78 into the insert position which in turn allows insertion spring 80 to operate the placement mechanisms within cassette player 70 to place cassette 9 in juxtaposition against tape head 74. Computer 16 will then interrogate senors to verify that cassette 9 has been loaded correctly. Detent arm switch 90 is used to tell computer 16 that the detent armature 50 has completed its traversal along transport member 22 and door open switch 92 is used to tell computer 16 that a cassette is presently within cassette player 70. Spindle sensor 98 will verify correct placement of cassette 9 within cassette player. After verifying correct placement of cassette 9, computer 16 will signal motor 68 to engage jointed members 66, 67 to force a clockwise motion upon shaft 72 thus forcing spindles 76, 77 into place. Once spindles 76, 77 engage cassette 9 the data recorded on cassette 9 can be read. Upon completion of reading cassette 9, computer 16 will signal motor 68 to force jointed members 66, 67 to force upon shaft 72 a two step counterclockwise motion. The first counterclockwise step exerted upon shaft 72 will disengage spindles 76, 77 from cassette 9. The second counterclockwise motion will force post 82 around the right angle contained within slot 79. This allows ejection spring 81 to exert a spring force on cassette armature 78 that places armature 78, and all placement mechanisms of cassette player 70 in an unloaded position. Cassette 9 will then be forced out of cassette player 70 and onto transport member 22.

Once analysis of single cassette tape 9 is finished and cassette 9 is ejected, cassette removal means consisting of cam mounted armatures 62, 63, attached in assembly with detent armature 50 to worm nut 32, grip ejected cassette 9 and pull the cassette 9 from cassette player 70. Since pincher arms 62, 63, are attached in assembly with detent armature 50 and worm nut 32, they will move with detent armature in forward and reverse directions under the control of worm drive 30. Transport clearing means are provided by clearing solenoid 64 actuating clearing piston 65 to clear the ejected tape from transport member 22 and into restacking means 100. In order for pincher arms 62, 63 to not interfere with the ejection of single cassette tape 9, they are separated by roller bar 60 prior reaching the end of transport member 22 adjacent cassette player 70. Once worm drive system 30 begins to move worm nut 32 away from cassette player 70, roller bar 60 becomes disengaged from, and no longer separates, pincher arms 62, 63. Pincher arms 62, 63 will then engage and hold single cassette 9 upon the initial movement of worm nut 32 away from cassette player 70, and pull cassette 9 from cassette player 70 onto the transport member 22. Pincher arms 62, 63 release cassette 9 next to clearing solenoid 64 by having separation rails 46, 47 open pincher arms 62, 63. Clearing solenoid 64 is activated when door open sensor 92 within cassette player 70 is interrogated by analysis system 10 and is read false indicating that cassette tape 9 has been removed from cassette player 70, at which point clearing piston 65 within clearing solenoid 64 punches cassette tape 9 off transport member 22 and into restacking means 100.

Figure 4:
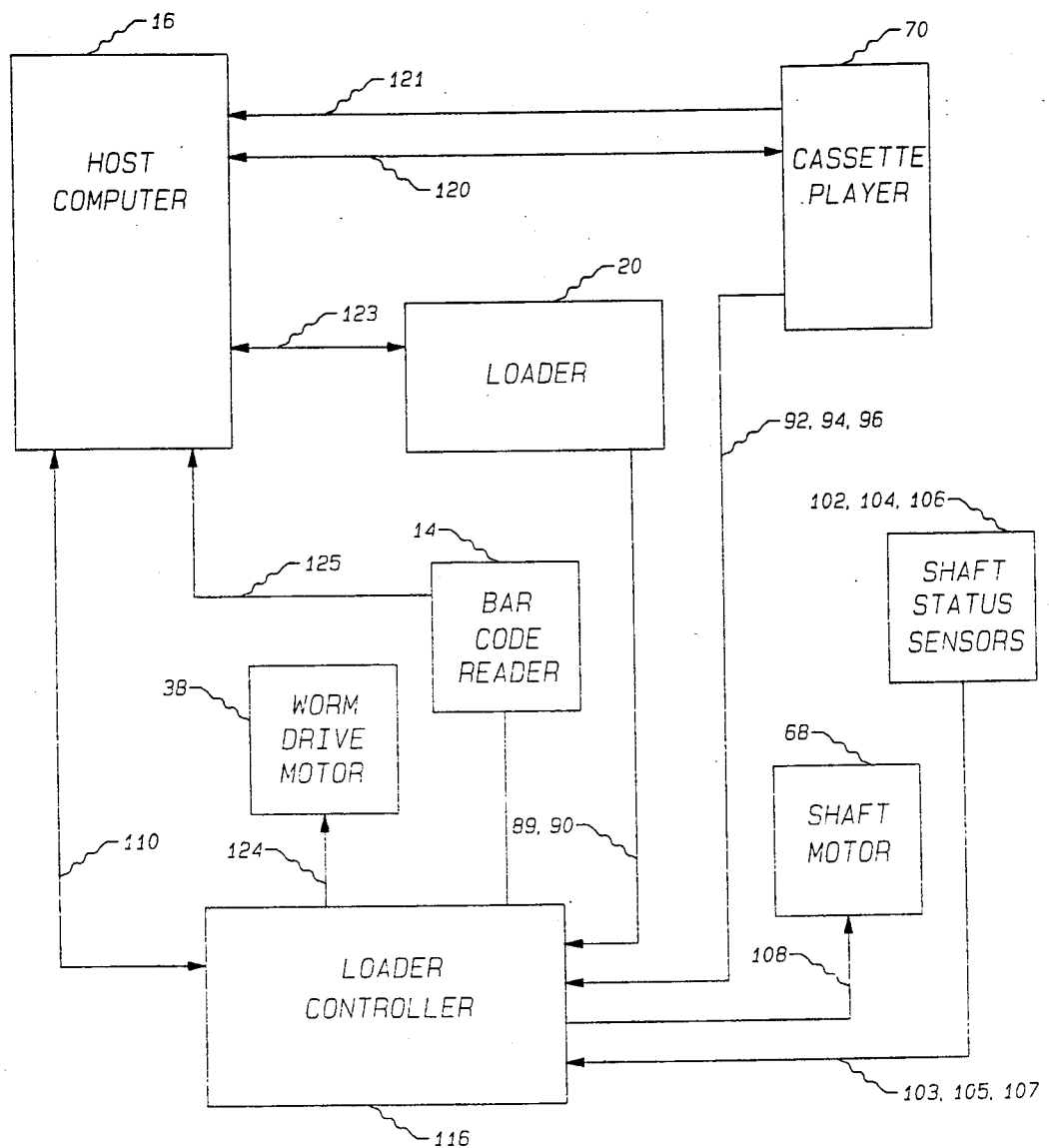
FIG. 4 is a block diagram showing the electrical interfaces within the system.

FIG. 4 shows a block diagram for the electrical connections within the analysis system of the preferred embodiment, it can best be understood by referring to FIG. 1 in conjunction with FIG. 4 The electrical interfaces seen in FIG. 4 operate as follows. Loader control 116 will await for the proper conditions which is signaled across the RS-232 control and status interface 110 with computer 16. Assuming that proper status to analyze tapes is given by computer 16, loader controller 116 will interrogate stack sensor 89 beneath stack holding means 26 to verify that at least one cassette is waiting within stack holding means 26. Bar code reader 14 will then in read bar code on the exterior of tape cassette 9 to positively identify patient and doctor. At this point computer 16 will instruct load controller 116 to initiate a cassette load sequence. The next action taken by the electrical system shown in FIG. 4, is for load controller to signal worm drive motor 38 to rotate in a first direction which will translate into a linear movement of detent armature 50 towards cassette player 70 accompanied by the repetitive reading of travel switch 90 by loader controller 116 until travel switch 90 reads positive when worm nut 32 travels the entire distance of transport member 22. Once travel switch 90 reads positive, loader controller 116 will read the shaft motor sensors 103, 105, and 107, prior to signaling shaft motor 68 the proper action to take. In loading a cassette into cassette player 70 the proper action is an instruction for shaft motor 68 to rotate shaft 72 in a clockwise manner. Once this instruction is executed cassette player 70 will then be ready to playback data recorded on the cassette tape 9. Computer 16 will receive this status across the RS-232 interface for control and status 125. As soon as cassette player 70 is ready for playback, computer 16 will signal cassette player 70 via the digital interface for tape motion control 120. In the preferred embodiment, three channels 1, 2, 3 of ECG recorded data and a timing channel 4 will be received from the cassette player 70 across tape signal interface 121 with computer 16. Typically, a timing signal 4 would be in the range of 32 Hz. The three channels 1, 2, 3 are analog signals. However, timing channel 4 is actually a sine wave at a predetermined frequency. Once cassette player 70 has completed transmission, it will signal this event to computer 16 on the tape motion control 120 interface. Computer 16 will then notify loader control 116, across the control and status interface 110, that an ejection sequence is to begin. Loader control 116 will then signal shaft motor 68 to rotate shaft 72 in a two step counterclockwise direction. Loader control 116 will read shaft status sensors 102, 104, and 106 (respectively up, middle and down shaft) for indications regarding the present position of jointed members 66, 67 and therefore shaft 72. Once shaft 72 has proceeded from up shaft status sensor 102, past middle shaft status sensor 104, where spindles 76, 77 disengage from cassette tape 9 to down shaft status sensor 106, the loader controller will signal the shaft motor 68 to stop turning. Load controller 116 will then signal worm drive motor 38 that an unloading cycle is now to take place. Worm drive motor 38 will then turn worm drive 30 to have worm nut 32 travel in a reverse direction away from cassette player 70. Once pincher armatures 62, 63 release cassette 9, door open switch 92 will be read false by loader controller 116 indicating that cassette 9 has cleared cassette player 70. Loader controller 116 will then signal solenoid 64 to fire piston 65 clearing cassette 9 into restacking means 100. The entire process is then repeated.

Figure 5:
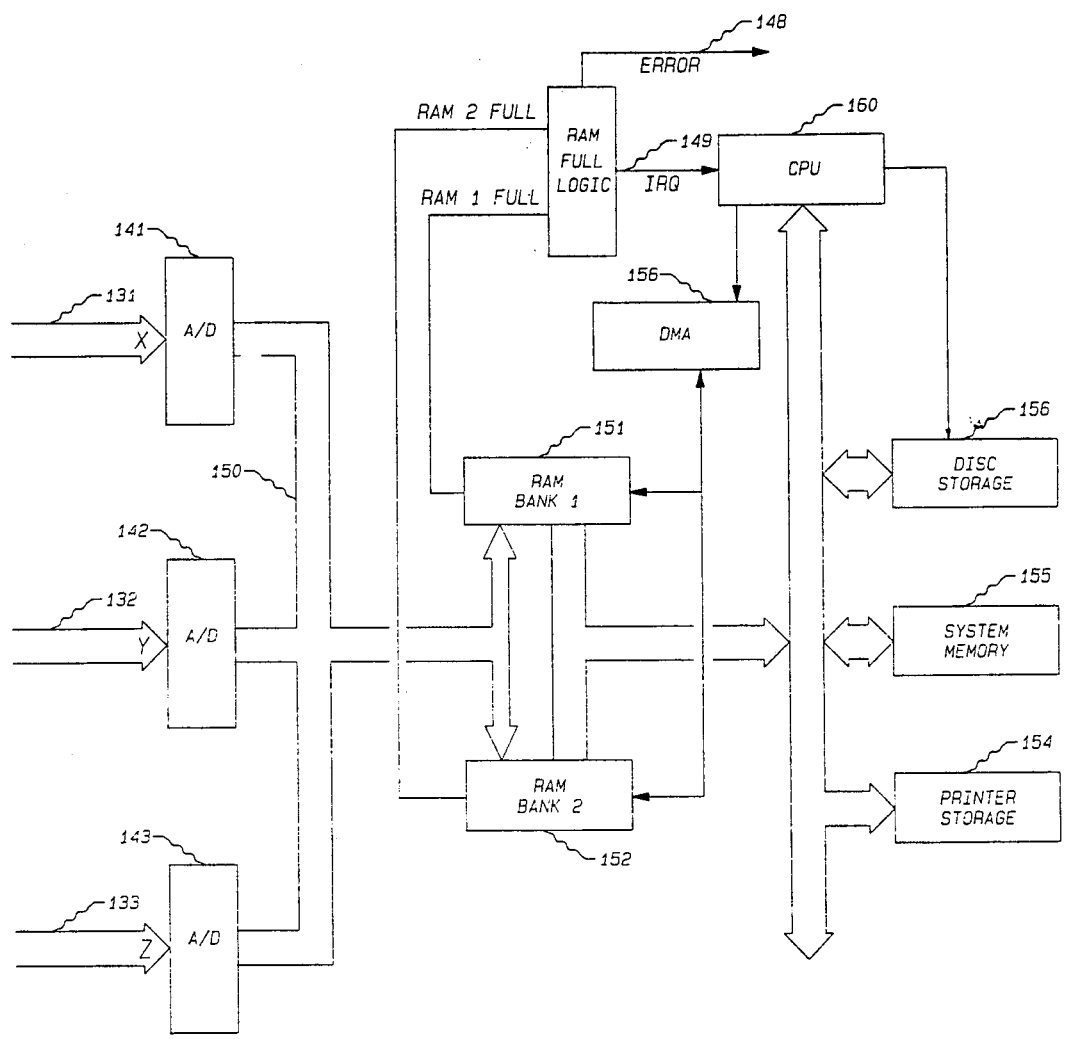
FIG. 5 is a block diagram of the analysis system.

The ECG analysis system, generally referred to as 10, can be seen in the block diagram shown in FIG. 5, will perform an arrhythmia analysis of the recorded data to identify the presence of clinically significant abnormalities. The preferred embodiment envisions a system employing analog magnetic tape, wherein it would be necessary to convert recorded data into a digital format. Digital Audio Tape (DAT) could equally be used in a system similar to the one disclosed, herein, DAT recordings would not require any form of digitizing, since a DAT cassette would already playback in a digital format. However, the preferred embodiment employs analog magnetic tape. The term playback means as used in the present application for invention is meant to designate all that is necessary to make recorded data available to a digital computer. In the preferred embodiment, playback means would therefore include the three A/D convertors 141, 142, 143. Here it can be seen that data is received via cassette player 70, as stated above, along tape signal interface 121. Each of the ECG channels 1, 2, 3 is taken from interface 121 and placed onto an Analog to digital input line 131, 132 or 133 to be transmitted to a separate analog to digital convertor 141, 142, or 143. The output of A/D convertors 141, 142, 143 is an 8-bit byte that is stored in either ram bank 1 151 or ram bank 2 152. It is envisioned that ram banks 151, 152 be designed in a ping-pong arrangement, enabling simultaneous read and write operations. However, numerous other arrangements are equally feasible. DMA 156 will control the reading of ram banks 151, 152 into system memory 155 from where CPU 160 can place the data into disc storage 158. Data may then be read by the CPU 160 directly from disc storage 158 for analysis or output by CPU 160 to printer 154.

Figure 6:
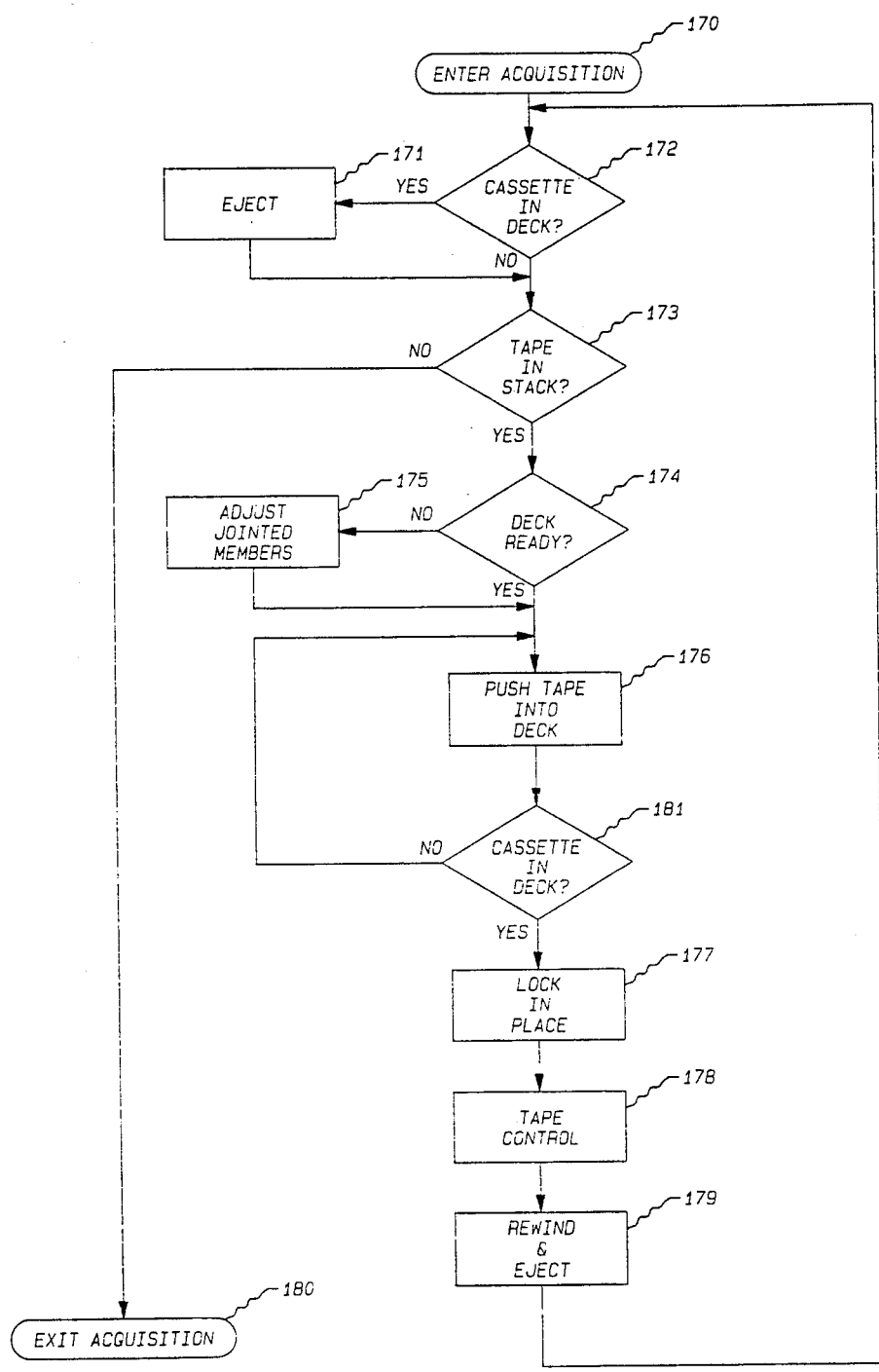
FIG. 6 is a flow-chart diagram illustrating the steps taken by the system in loading and unloading cassette tapes that are to be analyzed.

FIG. 6 illustrates the acquisition module 170, in flow chart form, wherein the system computer 16 executes the necessary steps to load and unload ECG cassette tapes into the multiple cassette loader 20. Initially cassette in deck 172 checks cassette player 70 for cassettes that have not been ejected. If cassette in deck 172 is found to be true (yes) then eject 171 is executed to remove the cassette tape from cassette player 70. Once it is certain that no cassettes are within cassette player 70, tape in stack 173 will check the stack sensor 89 for cassette to be analyzed. If there are no cassettes within the stack holding means 26 the computer 16 exits acquisition 180. If cassettes are within stack holding means deck ready 174 will verify that shaft sensors 102, 104, and 106 indicate proper positioning of shaft 72. Adjust jointed members 175 will correct any improper placement of shaft 72. At this point push tape into deck 176 will initiate the movement of detent armature 50 under control of worm drive 30 and continue this movement until cassette in deck 181 reads true. Cassette in deck 181 will be read true by a combination of travel 90, door open 92 and tape mechanism 9 4 switches all being true. Lock in place 177 will engage variable speed spindles 76, 77 and verify that the engagement is correct by interrogating spindle sensor 98. Tape control 178 will play the cassette tape 9 until the recorded data has been read. Once reading is complete rewind and eject 179 will rewind the cassette and eject it from cassette player 70. This entire cycle is repeated for each cassette contained within stack holding means 26 until tape in stack 173 reads false, at which point exit acquisition 180 is executed.

Figure 7:
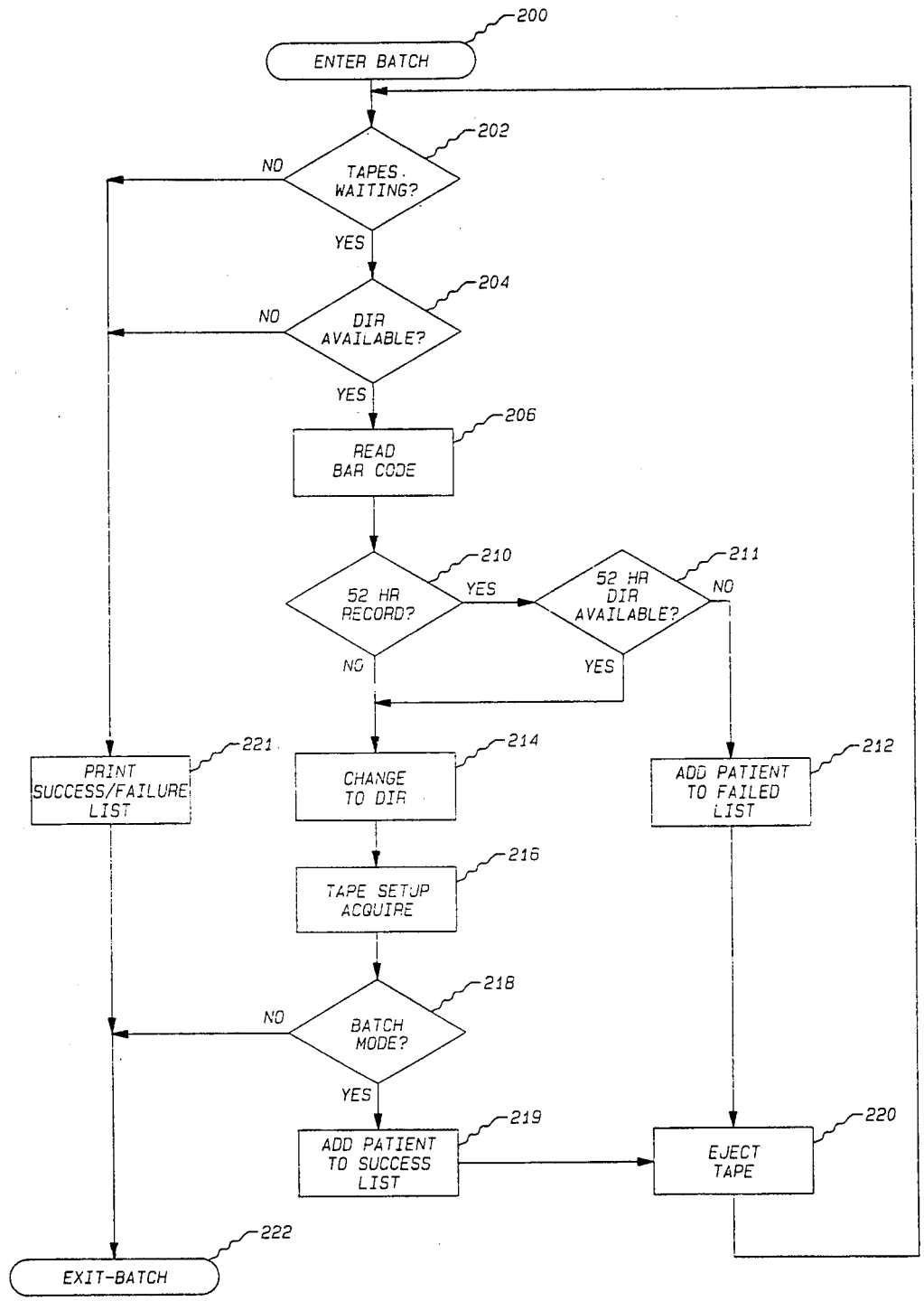
FIG. 7 is a flow-chart diagram illustrating the batch mode process that is run by the system.

Referring to FIG. 7, which is a flow diagram of the batch mode process executed by the present invention, seen is a process that is executed not on the multiple cassette loader 20 as in FIG. 6, but instead a process which is executed on computer 16 to organize the data retrieved from the multiple cassette tapes. Certain functions are similar to those previously discussed. Tape waiting 202 is indicative of cassettes existing within the stack holding means 26 waiting to be analyzed. Once cassettes are identified waiting to be analyzed, dir available 204 checks to see if directory space on the hard disc is available to store patient data. A true response to dir available 204 has the computer read bar code 206. The bar code will identify extra long tapes to 52 hr. record 210, a true response to which will then check for 52 Hr. Dir available 211. In situations where there is a 52 hour recording to be analyzed and there is no 52 directory space available, then add patient to failed list 212 will record the fact that this cassette was not analyzed and 220 will eject the cassette. If the cassette contains a 52 record 210 and 52 Hr dir available 211 reads true, or if the cassette is not a 52 hour recording, then change to DIR 214 is executed to make the computer 16 operating system look at the directory selected for the data contained on the cassette tape. Tape setup acquire 216 will then perform all necessary steps in reading data from the cassette. If batch is selected, as is the present case, then the patient must be added to success list 219, followed by eject tape 220 and the process starts over again. If tapes waiting 202 is false indicating no cassettes within the stack holding means 26 or dir available 204 is false, then print success/failure list 221 will generate a report of those cassettes tested prior to exit batch 222 being executed. A report is generated for each patient recording to enable those patient recordings containing benign ECG data to be segregated from those that require further analysis.

While the DETAILED DESCRIPTION OF THE PREFERRED EMBODIMENT has described the present invention with sufficient detail to enable those skilled in the relevant arts to make and use the invention, various changes, substitutions and alterations should be apparent to those so skilled that such obvious modifications can be made without departing from the spirit and scope of the invention.

We claim:

1. A system for classifying multiple electrocardiographic patient recordings comprising:
    an electrocardiographic (ECG) analysis system having computational means that executes an arrhythmia analysis algorithm capable of identifying significant cardiac abnormalities within ECG recordings on cassette tape and producing a report, thereof;
    playback means electrically connected to said ECG analysis system to accept cassette tapes and make ECG data, recorded thereon, available to said ECG analysis system;
    stack holding means for holding a plurality of cassette tapes;.

juxtaposition means for individual alignment of said plurality of cassette tapes with said playback means to enable reading of data stored on said plurality of cassette tapes;

removal means to remove said plurality of cassette tapes from alignment with said playback means at a predetermined time; and restacking mean for holding said plurality of cassette tapes after being analyzed.

2. The invention defined by claim 1 wherein said juxtaposition means further comprises insertion means consisting of a transfer rail having a slot through which detent armature means extend through said slot to individually slide each of said recordings from said stack holding means into juxtaposition within said playback means.

3. The invention defined by claim 2 where said insertion means further comprises a worm drive system geared to said detent armature means by a linkage, said linkage being constructed to extend said detent armature means when said worm drive is traveling in a first direction, thereby, enabling engagement of a single cassette within said stack holding means, and to retract said detent armature when said worm drive is traveling in a second direction, thereby, not engaging any cassettes within said stack holding means.

4. The invention defined by claim 3 wherein said removal means further comprises:

a pair of jointed members attached to ejection motor means to operate said ejection means within said playback means; and a pair of cam mounted armatures rotatably mounted to said insertion means to attach and hold said single cassette once ejected from said playback means.

5. The invention of claim 1 wherein said playback means further includes means for reading ECG tapes at various speeds, where at least one of said speeds is an accelerated speed capable at reading recorded data many times the real time recording rate.

6. The invention of claim 5 wherein said playback means further includes engagement means to firmly place said cassette against tape head means within said playback means such that said cassette may be played at many times the recording speed.

7. In an electrocardiographic (ECG) analysis system having computational means, an arrhythmia analyzer, playback means, means for automatically detecting an occurrence of clinically significant cardiac abnormalities, and means for creating a patient report delineating said occurrence of clinically significant abnormalities, the improvement comprising:

an automatic tape cassette loader, said loader having means for stacking a plurality of cassette tapes, insertion means to place said tapes into said playback means for analysis, removal means to take said tapes from said playback after said analysis, means for restacking said cassettes after analysis and means for individually identifying each of said plurality of cassette tapes.

8. The invention of claim 7 further comprising a sensor operative to indicate whether at least one cassette is within said means for stacking cassette tapes.

9. The invention of claim 7 further comprising a sensor operative to indicate whether a cassette tape is located within said playback means.

10. The invention of claim 7 wherein said means for individually identifying each of said plurality of cassette tapes comprises a bar code reader.

11. The invention of claim 10 further comprising means for transferring data received by said bar code reader to said means for creating patient reports of cardiac abnormalities.

12. A system for analyzing multiple electrocardiographic (ECG) cassette tape recordings comprising:

a digital computer having arrhythmia analysis means;

playback means being electrically connected to said digital computer for retrieving data stored on cassette tape and outputting data compatible with said digital computer;

multiple cassette loader means consisting of an elongated, rigid transport member having a first end immediately adjacent to said playback means, and having a longitudinal transport slot cut through said transport member;

cassette stack holding means fixedly attached near a second end of said transport member for holding a plurality of cassette tapes;

cassette placement means being physically connected to said loader means by a worm drive system and electrically connected to said digital computer, said placement means consisting of a detent armature mounted said worm drive system, said detent armature protruding through said transport slot to engage a single cassette within said stack means and transport said single cassette along the longitudinal axis of said transport slot and into said playback means under control of worm drive motor means, said worm drive motor means having a control mechanism controlled by said digital computer;

cassette removal means comprising of a pair of jointed members cooperatively coupled to removal motor means and an ejection mechanism within said playback means, said cassette removal means operative to eject said cassette from said playback means at a predetermined time, said cassette removal means further comprising a pair of cam mounted armatures, attached in assembly and operating in cooperation with said placement means for attaching to said cassette once ejected from said playback means and pulling said cassette onto said transport member; and transport member clearing means for removal of ejected cassettes from said transport slot; and control means with said digital computer to control said placing means and said removal means.

13. The invention of claim 12 wherein said predetermined time of ejection of said cassette is determined by said computer in response to signals received from said playback means.

14. The invention of claim 12 wherein said detent armature is geared by a four bar linkage system.

15. The invention of claim 12 wherein said playback means further includes means for reading recorded data at various speeds, including at least one speed that reads recorded data at many times faster than recorded.

16. A cassette tape analysis system having automatic tape loading, playing and removal features comprising:

an analysis system having computational means;

playback means, including analog to digital (A/D) conversion means for supplying said analysis system data recorded on a cassette tape;

an elongated, rigid transport member mounted with a first end of its longitudinal axis immediately adjacent to said playback means, said transport member having a slot throughout a substantial portion of said transport member's longitudinal axis;

a cassette stack retainer mounted near a second end of said transport member, said stack retainer capable of holding a plurality of cassette tapes;

a detent armature mounted on a worm drive, said detent armature extending through said slot to engage one of said cassette tapes within said cassette stack retainer, when activated by said worm drive in a forward direction, and push said cassette tape along said transport member into said playback means, said worm drive further being operative in a reverse direction to retract said detent armature towards said second end of said transport member, said detent armature being geared to retract at a predetermined position, thereby not engaging said plurality of cassette tapes contained within said cassette stack retainer while in said reverse direction.

17. The invention of claim 16 wherein said playback means has at least one sensor capable detecting when a cassette has been inserted into said playback means.

18. The invention of claim 16 wherein said transport member has a plurality of sensors to indicate when loading of said playback means should take place and when loading of said playback means is accomplished.

19. The invention of claim 16 further including restacking means to hold ejected cassettes after they have been cleared from said transport member.

* * * * *